United States Patent
Park et al.

(10) Patent No.: US 9,968,334 B2
(45) Date of Patent: May 15, 2018

(54) ULTRASOUND DIAGNOSTIC METHOD AND APPARATUS USING SHEAR WAVES

(71) Applicant: Samsung Electronics Co., Ltd., Suwon-si, Gyeonggi-do (KR)

(72) Inventors: Jun-ho Park, Hwaseong-si (KR); Ki-wan Choi, Anyang-si (KR); Hyoung-ki Lee, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 315 days.

(21) Appl. No.: 14/341,255

(22) Filed: Jul. 25, 2014

(65) Prior Publication Data

US 2015/0032000 A1 Jan. 29, 2015

(30) Foreign Application Priority Data

Jul. 29, 2013 (KR) .................. 10-2013-0089826

(51) Int. Cl.
| | |
|---|---|
| *A61B 8/08* | (2006.01) |
| *G01S 7/52* | (2006.01) |
| *B06B 1/06* | (2006.01) |
| *G10K 11/34* | (2006.01) |

(Continued)

(52) U.S. Cl.
CPC ............ *A61B 8/485* (2013.01); *A61B 8/08* (2013.01); *A61B 8/4488* (2013.01); *A61B 8/565* (2013.01); *B06B 1/0622* (2013.01); *G01S 7/52042* (2013.01); *G10K 11/34* (2013.01); *A61B 8/00* (2013.01); *A61B 8/4405* (2013.01); *A61B 8/4472* (2013.01); *A61B 8/469* (2013.01);

(Continued)

(58) Field of Classification Search
CPC ........... A61B 8/00; A61B 8/08; A61B 8/4405; A61B 8/4472; A61B 8/4488; A61B 8/469; A61B 8/485; A61B 8/565; B06B 1/0622; B06B 2201/76; G01S 15/8915; G01S 7/52022; G01S 7/52042; G10K 11/34

See application file for complete search history.

(56) References Cited

U.S. PATENT DOCUMENTS

| | | |
|---|---|---|
| 7,252,004 B2 | 8/2007 | Fink et al. |
| 8,647,276 B2 | 2/2014 | Tabaru et al. |

(Continued)

FOREIGN PATENT DOCUMENTS

| | | |
|---|---|---|
| KR | 10-2012-0131552 | 12/2012 |
| WO | WO 2008/141220 | 11/2008 |

(Continued)

OTHER PUBLICATIONS

P. Song et al., "Comb-Push Ultrasound Shear Elastography (CUSE): A Novel Method for Two-Dimensional Shear Elasticity Imaging of Soft Tissues," *IEEE Transactions on Medical Imaging*, vol. 31, No. 9, Sep. 2012, pp. 1821-1832.

(Continued)

*Primary Examiner* — Katherine Fernandez
(74) *Attorney, Agent, or Firm* — Staas & Halsey LLP

(57) ABSTRACT

An ultrasound diagnostic method and apparatus determines a transmission condition for generating shear waves at two or more positions of an object, for each of a plurality of elements of a transducer, and generates an ultrasound signal transmitted to the object through a full aperture of the transducer, according to the transmission condition.

26 Claims, 7 Drawing Sheets

(51) Int. Cl.
  *A61B 8/00* (2006.01)
  *G01S 15/89* (2006.01)
(52) U.S. Cl.
  CPC ....... *B06B 2201/76* (2013.01); *G01S 7/52022* (2013.01); *G01S 15/8915* (2013.01)

(56) References Cited

U.S. PATENT DOCUMENTS

| | | | |
|---|---|---|---|
| 2010/0168566 A1* | 7/2010 | Bercoff | A61B 8/08 600/438 |
| 2012/0136250 A1* | 5/2012 | Tabaru | A61B 8/08 600/438 |
| 2012/0158323 A1 | 6/2012 | Hazard et al. | |
| 2012/0302883 A1* | 11/2012 | Kong | A61N 7/02 600/439 |
| 2013/0031981 A1 | 2/2013 | Montaldo et al. | |
| 2013/0051178 A1 | 2/2013 | Rybyanets | |
| 2013/0144165 A1* | 6/2013 | Ebbini | A61B 8/4488 600/439 |
| 2014/0024943 A1* | 1/2014 | Nicolas | G01S 15/8959 600/447 |

FOREIGN PATENT DOCUMENTS

| | | |
|---|---|---|
| WO | 2011/027644 | 3/2011 |
| WO | WO 2012/116364 | 8/2012 |

OTHER PUBLICATIONS

M. Tanter et al., "Quantitative Assessment of Breast Lesion Viscoelasticity: Initial Clinical Results Using Supersonic Shear Imaging," *Ultrasound in Medicine & Biology*, vol. 34, No. 9, Feb. 8, 2008, pp. 1373-1386.

W. F. Walker, "Internal deformation of a uniform elastic solid by acoustic radiation force," *Journal of the Acoustical Society of America*, vol. 105, No. 5, Apr. 1999, pp. 2508-2518.

European Search Report dated Jan. 21, 2015 from European Patent Application No. 14178861.2, 8 pages.

Turnbull et al., "Beam Steering with Pulsed Two-Dimensional Transducer Arrays", IEEE Transactions on Ultrasonics, Ferroelectrics and Frequency Control, vol. 38, No. 4, Jul. 4, 1991, pp. 320-333.

Hazard et al., "Integration of Crawling Waves in an Ultrasound Imaging System. Part 1: System and Design Considerations", Ultrasound in Medicine and Biology, vol. 38, No. 2, 2012, pp. 296-311.

Korean Office Action dated May 2, 2016, from Korean Patent Application No. 10-2013-0089826, 10 pages (including partial translation).

$2^{nd}$ Korean Office Action dated Nov. 28, 2016 in corresponding Korean Patent Application No. 10-2013-0089826 (3 pages) (3 pages English Translation).

$3^{rd}$ Korean Office Action dated Jan. 24, 2017 in corresponding Korean Patent Application No. 10-2013-0089826 (3 pages) (3 pages English Translation).

\* cited by examiner

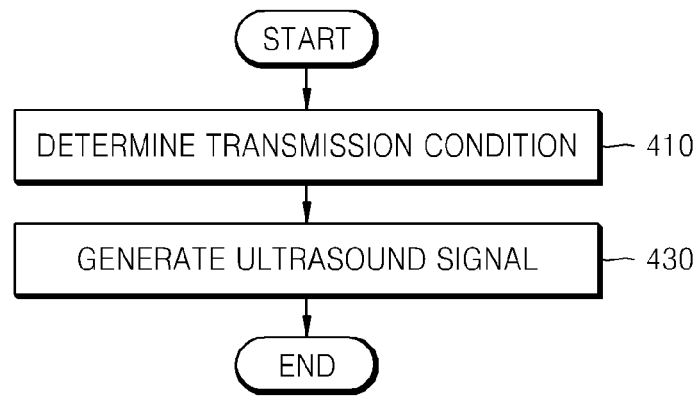
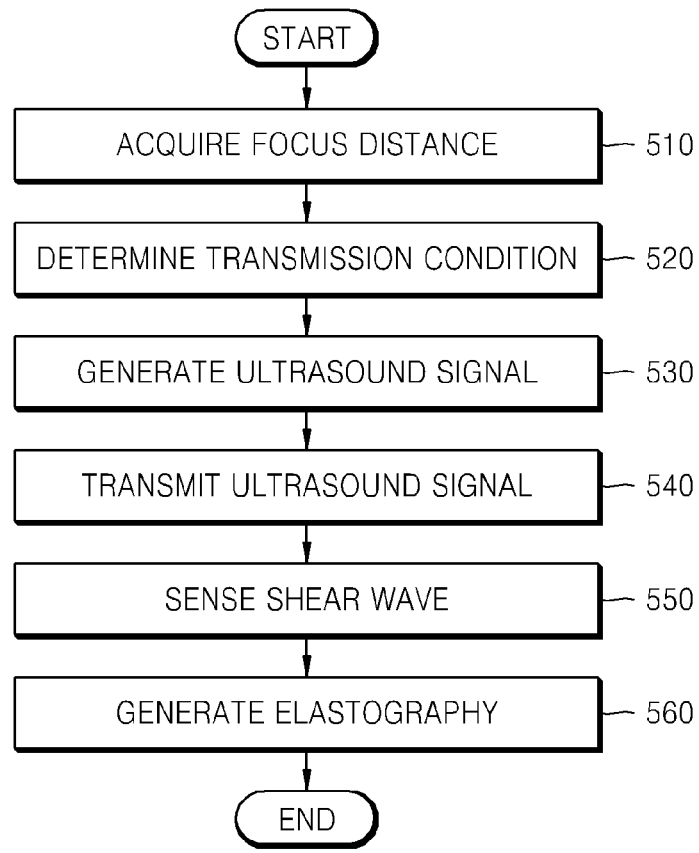

ULTRASOUND DIAGNOSTIC METHOD AND APPARATUS USING SHEAR WAVES

CROSS-REFERENCE TO RELATED APPLICATIONS

This application claims the benefit of Korean Patent Application No. 10-2013-0089826, filed on Jul. 29, 2013, in the Korean Intellectual Property Office, the disclosure of which is incorporated herein in its entirety by reference.

BACKGROUND

1. Field

One or more embodiments disclosed herein relate to a method and apparatus that use shear waves in diagnosing an object with ultrasound waves.

2. Description of the Related Art

Ultrasound diagnostic apparatuses transmit an ultrasound signal (generally, about 20 kHz or more) to an internal part of an object by using a probe, and obtain an image of the internal part of the object by using information of an echo signal reflected from the object. Generally, the ultrasound diagnostic apparatuses may be used for the medical purpose of observing the inside of an object, detecting a foreign material, and assessing an injury. The ultrasound diagnostic apparatuses may be more stable than diagnostic apparatuses using X-rays, display an image in real time, and are generally considered safe because there is no exposure to radioactivity, and thus may be widely used along with other image diagnostic apparatuses.

The ultrasound diagnostic apparatuses may generate an elastography image that is obtained by observing a difference between motions of an object before and after applying a pressure to the inside of the object. In elastography, a stiff tissue is generally expressed with a dark color, and a smooth tissue is expressed with a bright color. Therefore, it is possible to determine or diagnose whether an internal tumor or lump of an object is positive or negative even without a tissue examination, and thus, a diagnostic result is quickly acquired, and the diagnostic cost is reduced.

SUMMARY

One or more embodiments of the disclosure include an ultrasound diagnostic method and apparatus that diagnose an object by using shear waves.

One or more embodiments of the disclosure include a computer-readable storage medium storing a program for executing the ultrasound diagnostic method in a computer.

Additional aspects will be set forth in part in the description which follows and, in part, will be apparent from the description, or may be learned by practice of the presented embodiments.

According to one or more embodiments of the disclosure, an ultrasound diagnostic method using shear waves includes determining a transmission condition for generating shear waves at two or more positions of an object, for each of a plurality of elements of a transducer, and generating an ultrasound signal transmitted to the object through a full aperture of the transducer, according to the transmission condition.

The determining may include determining the transmission condition for simultaneously generating the shear waves at the two or more positions of the object.

The ultrasound diagnostic method may further include acquiring information on a focus distance from a surface of the object to a position at which each of the shear waves is generated, wherein the determining may include determining the transmission condition in consideration of the information on the focus distance.

The transmission condition may include at least one of a level, phase, and delay time of the ultrasound signal.

The determining may include determining the transmission condition on a basis of a position of a corresponding element in the full aperture.

The determining may include determining the transmission condition on a basis of a function of a plurality of vectors indicating a displacement from each element to a position at which each of the shear waves is generated.

The determining may include determining the transmission condition by using a pseudo inverse matrix of a matrix expressing the function.

The ultrasound diagnostic method may further include transmitting the ultrasound signal to the object, and sensing the shear waves generated at the two or more positions.

The sensing may include transmitting a plane wave to the object, and receiving an echo signal for the plane wave.

The ultrasound diagnostic method may further include measuring a physical characteristic of the object on a basis of the sensed shear waves, and generating an elastography of the object on a basis of the physical characteristic.

The physical characteristic may include a traveling speed of each of the shear waves.

According to one or more embodiments of the disclosure, an ultrasound diagnostic apparatus for diagnosing an object with shear waves may include a transmission condition calculator that determines a transmission condition for generating shear waves at two or more positions of an object, for each of a plurality of elements of a transducer, and a pulse generator that generates an ultrasound signal transmitted to the object through a full aperture of the transducer, according to the transmission condition.

According to one or more embodiments of the disclosure, provided is a non-transitory computer-readable storage medium storing a program for executing the ultrasound diagnostic method.

According to one or more embodiments of the disclosure, an ultrasound diagnostic apparatus to diagnose an object by using shear waves may include a probe comprising a transducer including a plurality of elements, a transmission condition calculator to determine a transmission condition of an ultrasound signal to be transmitted through a full aperture of the transducer, to simultaneously generate shear waves at two or more focus positions of an object, and a pulse generator to generate the ultrasound signal to be transmitted to the object through the full aperture of the transducer, using the determined transmission condition.

The transmission condition calculator may determine the transmission condition as a function of a plurality of displacement vectors from n number of elements to an mth focus position, n denoting a number of elements in the transducer and m denoting a number of focus positions in the object.

The transmission condition calculator may determine a different transmission condition for each of the plurality of elements. The transmission condition calculator may determine the transmission condition based on a position of each of the plurality of elements in the full aperture of the transducer, and set a coefficient for each element based on an element position, the transmission condition being determined based on a value of the coefficient.

A first coefficient may be set for a first group of elements of the transducer and the first coefficient may also be set for a second group of elements of the transducer, and a second coefficient may be set for a third group of elements of the transducer, the second coefficient being lower than the first coefficient. The ultrasound diagnostic apparatus may adjust the coefficient to adjust at least one of a distance between focuses and a depth at which a multi-focus is formed.

BRIEF DESCRIPTION OF THE DRAWINGS

These and/or other aspects will become apparent and more readily appreciated from the following description of the embodiments, taken in conjunction with the accompanying drawings of which:

FIG. 4 is a flowchart illustrating an ultrasound diagnostic method according to an embodiment of the disclosure;

FIG. 5 is a flowchart illustrating an ultrasound diagnostic method according to another embodiment of the disclosure;

DETAILED DESCRIPTION

Figure 1:
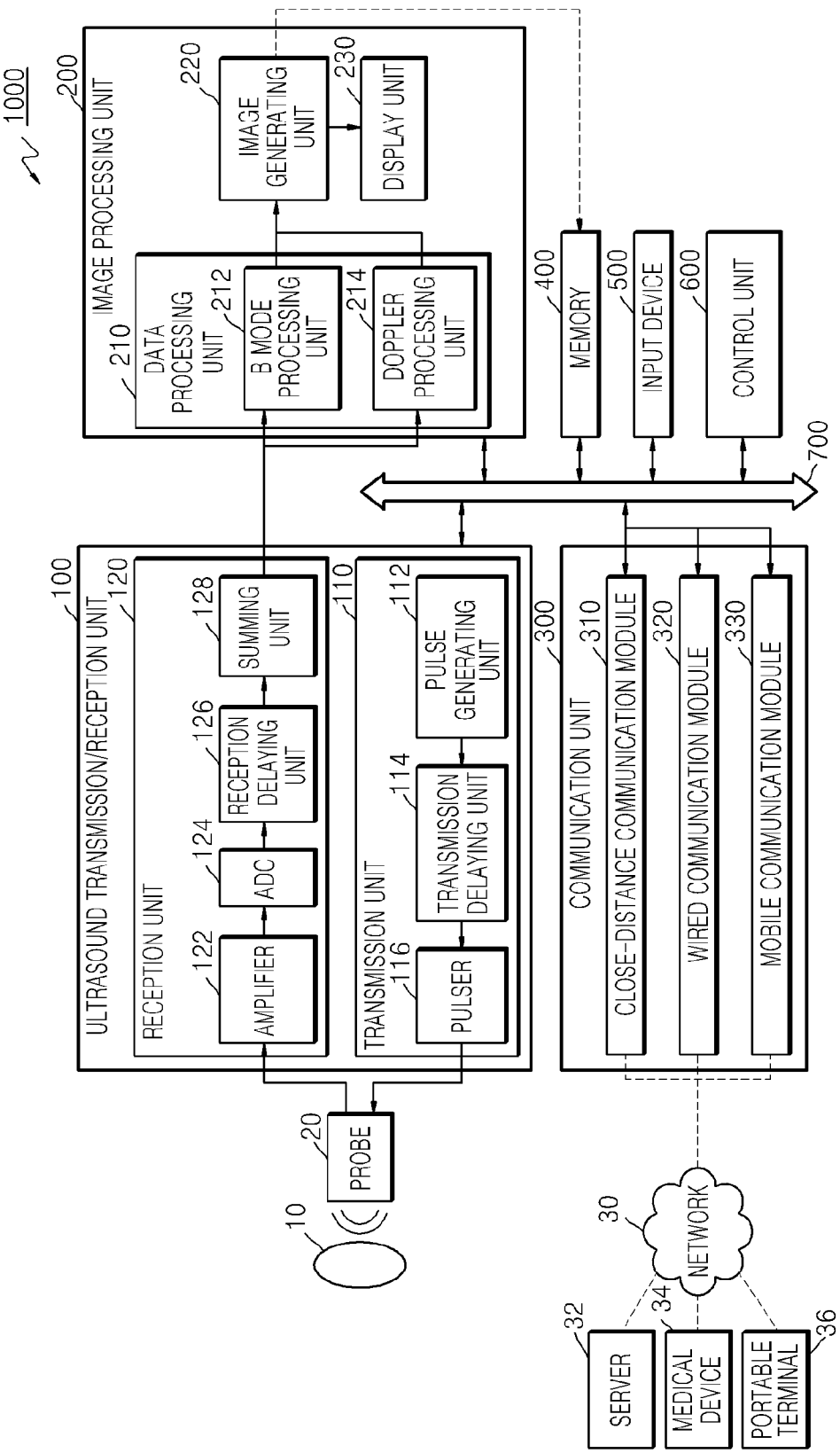
FIG. 1 is a block diagram illustrating a configuration of an ultrasound diagnostic apparatus relevant to an embodiment of the disclosure.

Reference will now be made in detail to embodiments, examples of which are illustrated in the accompanying drawings, wherein like reference numerals refer to like elements throughout. In this regard, the example embodiments may have different forms and should not be construed as being limited to the descriptions set forth herein. Accordingly, the embodiments are merely described below, by referring to the figures, to explain aspects of the disclosure. As used herein, the term "and/or" includes any and all combinations of one or more of the associated listed items. Expressions such as "at least one of," when preceding a list of elements, modify the entire list of elements and do not modify the individual elements of the list.

Terms used in the disclosure have been selected as general terms which are widely used by those of ordinary skill in the art, in consideration of the functions of the disclosure, but may be altered according to the intent of an operator skilled in the art, conventional practice, or introduction of new technology. Also, if there is a term which is arbitrarily selected by the applicant in a specific case, the meaning of the term will be described in detail in a corresponding description portion of the disclosure. Therefore, the terms should be defined or understood on the basis of the entire content of the disclosure, instead of a simple name of each of the terms.

In this disclosure, when it is described that one comprises (or includes or has) some elements, it should be understood that it may comprise (or include or has) only those elements, or it may comprise (or include or have) other elements as well as those elements if there is no specific limitation. The term "module", as used herein, means, but is not limited to, a software or hardware component, such as a Field Programmable Gate Array (FPGA) or an Application Specific Integrated Circuit (ASIC), which performs certain tasks. A module may advantageously be configured or arranged to reside in an addressable storage medium and configured to (adapted to, suitable for, capable of, operable to, arranged to, etc.) execute on one or more processors.

Thus, a module may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality provided for in the components and modules may be combined into fewer components and modules or further separated into additional components and modules.

For example, a processing device may be implemented using one or more general-purpose or special purpose computers, and may include, for example, one or more of a processor, a controller and an arithmetic logic unit, a central processing unit (CPU), a graphics processing unit (GPU), a digital signal processor (DSP), a microcomputer, a field programmable array, a programmable logic unit, an application-specific integrated circuit (ASIC), a microprocessor or any other device capable of responding to and executing instructions in a defined manner.

The term "image" as used herein may denote multi-dimensional data composed of discrete image factors (for example, pixels in a two-dimensional (2D) image and pixels in a three-dimensional (3D) image). For example, an image may include a medical image of an object which is acquired by an X-ray apparatus, a computed tomography (CT) apparatus, a magnetic resonance imaging (MRI) apparatus, an ultrasound apparatus, or another medical image photographing apparatus.

The term "object" or "examinee" as used herein may generally include any kind of object, including a person, an animal, a part of the person, or a part of the animal. For example, an object may include an organ such as a liver, a heart, a womb, a brain, breasts, an abdomen, or the like, or a blood vessel. Also, the term "object" may include a phantom. The phantom denotes a material having a volume very close to a density of organisms and an effective atomic number, and may include a spherical phantom having a temper similar to a human body.

The term "user" as used herein may generally include any user, for example, a person. For example the user may be a medical expert, a doctor, a nurse, a medical technologist, a medical image expert, or the like, or may be an engineer repairing a medical apparatus. However, the user is not limited thereto.

Hereinafter, embodiments of the disclosure will be described in detail to be easily understood by those of ordinary skill in the art with reference to the accompanying drawings. The disclosure may, however, be embodied in many different forms and should not be construed as being limited to the embodiments set forth herein. In the accompanying drawings, a portion irrelevant to a description of the disclosure will be omitted for clarity.

FIG. 1 is a block diagram illustrating a configuration of an ultrasound diagnostic apparatus 1000 relevant to an embodiment of the disclosure. Referring to FIG. 1, the ultrasound diagnostic apparatus 1000 may include a probe 20, an ultrasound transceiver 100, an image processor 200, a communicator 300, a memory 400, an input device 500, and a controller 600. One or more, or all of the above-described elements may be connected to each other through a bus 700, for example. The above-described elements may be connected to each other through a wired or wireless network, or a combination thereof.

The ultrasound diagnostic apparatus 1000 may be implemented as a portable type as well as a card type. Examples of the portable diagnostic apparatuses may include picture archiving and communication system (PACS) viewers, smartphones, laptop computers, personal digital assistants (PDAs), tablet personal computers (PCs), etc., but are not limited thereto.

The probe 20 may transmit an ultrasound signal to an object 10 according to a driving signal applied from the ultrasound transceiver 100, and receives an echo signal reflected from the object 10. The probe 20 may include a plurality of transducers, which vibrate according to the applied driving signal to generate an ultrasound wave that is acoustic energy. Also, the probe 20 may be connected to a body of the ultrasound diagnostic apparatus 1000 in a wired or wireless manner, and the ultrasound diagnostic apparatus 1000 may include a plurality of the probes 20 depending on an implementation type.

An ultrasound transmission unit 110 may supply the driving signal to the probe 20, and may include a pulse generator 112 (pulse generating unit), a transmission delayer 114 (transmission delaying unit), and a pulser 116. The pulse generator 112 may generate a pulse used to generate a transmission ultrasound wave based on a pulse repetition frequency (PRF). The transmission delayer 114 may apply a delay time, used to determine a transmission directionality, to the pulse. A plurality of the pulses with the delay time applied thereto may respectively correspond to a plurality of piezoelectric vibrators included in the probe 20. The pulser 116 may apply a driving signal (or a driving pulse) to the probe 20 at a timing which corresponds to each of the plurality of rate pulses with the delay time applied thereto.

A reception unit 120 may process a signal received from one or more of the plurality of transducers disposed in the probe 20, to generate ultrasound data, and may include an amplifier 122, an analog-to-digital converter (ADC) 124, a reception delayer 126 (reception delaying unit), and an adder 128 (summing unit). The amplifier 122 may amplify an echo signal for each channel, and the ADC 264 analog-to-digital may convert the amplified echo signal. The reception delayer 126 may apply a delay time, used to decide a reception directionality, to the converted signal. The adder 128 may add the signals processed by the reception delayer 126 to generate ultrasound data. The reception unit 120 may not include the amplifier 122 depending on an implementation type. For example, if a sensitivity of the probe 20 is enhanced or the number of bits processed by the ADC 124 increases, the amplifier 122 may not be provided.

The image processor 200 may perform a scan conversion on the ultrasound data generated by the ultrasound transceiver 100 to generate and display an ultrasound image. The ultrasound image may display a motion of an object as a Doppler image that expresses a moving object by using the Doppler effect, in addition to a grayscale ultrasound image that is generated by scanning the object according to an A mode, a B mode, and a motion (M) mode, for example. The Doppler image may include a blood Doppler image (also called a color Doppler image) indicating a flow of blood, a tissue Doppler image indicating a motion of a tissue, and/or a spectral Doppler image that displays a moving speed of the object as a waveform.

A B mode processor 212 (B mode processing unit) may extract a B mode component from the ultrasound data to process a B mode component. An image generator 220 (image generating unit) may generate an ultrasound image that displays a signal intensity as a brightness, on the basis of the B mode component extracted by the B mode processor 212.

Similarly, a Doppler processor 214 (Doppler processing unit) may extract a Doppler component from the ultrasound data, and the image generator 220 may generate a Doppler image that displays a motion of an object as a color or a waveform, on the basis of the extracted Doppler component.

The image generator 220 according to an embodiment may perform a volume rendering operation on volume data to generate a 3D ultrasound image, and may also generate an elastography image that shows a degree of modification (for example, based on a pressure) of an object 10. Furthermore, the image generator 220 may express various pieces of additional information about the ultrasound image as texts and graphics. The generated ultrasound image may be stored in a memory 400.

A display unit 230 may display the generated ultrasound image. The display unit 230 may display various pieces of information processed by the ultrasound diagnostic apparatus 1000, in addition to the ultrasound image, on a screen through a graphics user interface (GUI). The ultrasound diagnostic apparatus 1000 may include two or more display units 230 depending on an implementation type. The display unit 230 may include one or more of a liquid crystal display (LCD), a light emitting diode (LED) display, an organic light emitting diode (OLED) display, active matrix organic light emitting diode (AMOLED), flexible display, 3D display, a plasma display panel (PDP), a cathode ray tube (CRT) display, and the like, for example. However, the disclosure is not limited thereto and may include other types of displays.

The communicator 300 (communication unit) may be connected to a network 30 in a wired or wireless manner or a combination thereof, to communicate with an external device or server. For example, the communicator 300 may exchange data with a hospital server or a medical apparatus of a hospital which is connected thereto through a medical image information system (e.g., a PACS). Also, the communicator 300 may perform data communication according to the digital imaging and communications in medicine (DICOM) standard.

The communicator 300 may transmit and receive data, such as an ultrasound image, ultrasound data, Doppler data, etc. of an object, associated with a diagnosis of the object, over the network 30, and may also transmit and receive a medical image captured by a medical apparatus such as a CT apparatus, a MRI apparatus, or an X-ray apparatus. Furthermore, the communicator 300 may receive information about a diagnosis history or treatment schedule of a patient from a server, and use a diagnosis of an object. In addition, the communicator 300 may perform data communication with a portable terminal of a doctor, a patient, or some other authorized entity or user, in addition to a server or medical apparatus of a hospital.

The communicator 300 may be connected to the network 30 in a wired or wireless manner, and may exchange data with a server 32, a medical apparatus (medical device) 34, or a portable terminal 36. The communicator 300 may include one or more elements that enable communication with an external device, and for example, may include a short-distance (close distance) communication module 310, a wired communication module 320, and a mobile communication module 330.

The short-distance communication module 310 may denote a module for short-distance communication within a certain distance or area. Short-distance communication technology, according to an embodiment of the disclosure, may include wireless LAN, Wi-Fi, Bluetooth, Zigbee, Wi-Fi direct (WFD), ultra wideband (UWB), infrared data association (IrDA), Bluetooth low energy (BLE), and near field communication (NFC), but the short-distance communication technology is not limited thereto.

The wired communication module 320 may denote a module for communication using an electrical signal or an optical signal. Wired communication technology according to an embodiment may include a pair cable, a coaxial cable, an optical fiber cable, an Ethernet cable, and the like.

The mobile communication module 330 may transmit and/or receive a radio frequency (RF) signal to and from a base station, an external terminal, and a server over a mobile communication network. Here, the RF signal may include various types of data based on transmission and reception of a voice call signal, a video call signal, a letter/multimedia message, and the like.

The memory 400 may store various pieces of information processed by the ultrasound diagnostic apparatus 1000. For example, the memory 400 may store medical data, such as input/output ultrasound data and ultrasound images, associated with a diagnosis of an object, and may also store an algorithm or a program which is executed in the ultrasound diagnostic apparatus 1000.

The memory 400 may be embodied as various kinds of storage mediums such as a flash memory, a hard disk, a nonvolatile memory device such as an electrically erasable programmable read only memory (EEPROM), a Read Only Memory (ROM), Programmable Read Only Memory (PROM), a USB drive, a volatile memory device such as a Random Access Memory (RAM), floppy disks, a blue-ray disk, or optical media such as CD ROM discs and DVDs, or combinations thereof. Also, the ultrasound diagnostic apparatus 1000 may operate a web storage facility or a cloud server which performs a storage function of the memory 400 on a web. However, examples of the memory 400 are not limited to the above description, and may be realized by other various devices and structures as would be understood by those skilled in the art.

The input device 500 may denote a device that receives data, used to control the ultrasound diagnostic apparatus 1000, from a user. The input device 500 may include one or more hardware elements (including combinations thereof) of a keypad, a mouse, a touch pad, a trackball, a jog switch, but the disclosure is not limited thereto. As another example, the input device 500 may further include various input devices such as an electrocardiogram (ECG) measurement module, a breath measurement sensor, a voice recognition sensor (e.g., including a microphone to receive a voice command), a gesture recognition sensor (e.g., to recognize gestures of a user including movements of a body part), a fingerprint recognition sensor, an iris recognition sensor, a depth sensor, a distance sensor, etc. The input device 500 may also include, for example, a joystick, a button, a switch, an electronic pen or stylus, an output sound device (e.g., a speaker), a remote controller, a portable (e.g., a cellular or smart) phone, a tablet PC, a pedal or footswitch, a virtual-reality device, and so on. The input device 500 may further include a haptic device to provide haptic feedback to a user. The input device 500 may also include a touch screen, for example. The input device 500 may also function simultaneously as or correspond to a display device including the display unit 230.

The controller 600 may control an overall operation of the ultrasound diagnostic apparatus 1000. That is, the controller 600 may control operations between the probe 20, the ultrasound transceiver 100, the image processor 200, the communicator 300, the memory 400, and the input device 500 which are illustrated in FIG. 1.

Some or all of the probe 20, the ultrasound transceiver 100, the image processor 200, the communicator 300, the memory 400, the input device 500, and the controller 600 may be operated by a software module, but are not limited thereto. Some of the above-described elements may be operated by a hardware module. Also, at least some of the ultrasound transceiver 100, the image processor 200, and the communicator 300 may be included in the controller 600, but are not limited to the implementation type.

Figure 2:
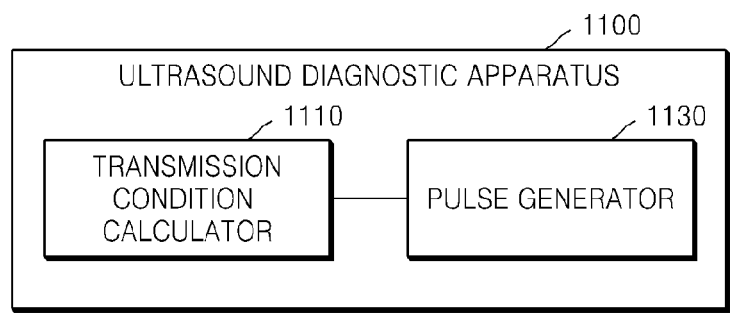
FIG. 2 is a block diagram illustrating a configuration of an ultrasound diagnostic apparatus according to an embodiment of the disclosure.

FIG. 2 is a block diagram illustrating a configuration or arrangement of an ultrasound diagnostic apparatus according to an embodiment of the disclosure. Referring to FIG. 2, an ultrasound diagnostic apparatus 1100 according to an embodiment of the disclosure may include a transmission condition calculator 1110 and a pulse generator 1130. A configuration of the ultrasound diagnostic apparatus 1100 is not limited to the illustrated details, and may be implemented as a type including more or less elements. For example, the ultrasound diagnostic apparatus 1100 may include some or all of the elements disclosed with respect to the ultrasound diagnostic apparatus 1000 of FIG. 1.

The transmission condition calculator 1110 may determine a transmission condition of an ultrasound signal that is transmitted by the ultrasound diagnostic apparatus 1100 in order for a shear wave to be generated in an object. The transmission condition calculator 1110 may determine a transmission condition for one or more or all of a plurality of elements included in a transducer of the ultrasound diagnostic apparatus 1100. That is, the transmission condition calculator 1110 may determine in which direction and at what intensity the ultrasound diagnostic apparatus 1100 transmits an ultrasound signal, and a transmission condition (transmission parameter) according to an embodiment may include a level, phase, and delay time of an ultrasound signal.

The transmission condition calculator 1110 may determine a transmission condition of an ultrasound signal that is used to generate a shear wave at two or more positions of an object. That is, the transmission condition calculator 1110 may determine a transmission condition of an ultrasound signal transmitted through a full aperture of the transducer, thereby simultaneously generating shear waves at two or more internal positions of the object. In other words, the transmission condition calculator 1110 may determine a transmission condition for simultaneously generating shear waves at internal multi focuses of an object.

A transmission condition calculator 1110 according to an embodiment of the disclosure may acquire information about a focus distance that corresponds to a distance from a surface of an object to a position at which a shear wave is generated, and may determine a transmission condition on the basis of the focus distance. The transmission condition calculator 1110 may acquire information about a focus distance from a received user input, or acquire the focus distance on the basis of an application that is selected for diagnosing an object. The embodiment will be described in detail with reference to FIG. 6.

The transmission condition calculator 1110 according to an embodiment of the disclosure may determine a transmission condition on the basis of a position of one or more or all of a plurality of elements in the full aperture of the transducer. That is, the transmission condition calculator 1110 may determine different transmission conditions for the respective elements, which will be described in detail with reference to FIG. 8.

The transmission condition calculator 1110 according to an embodiment of the disclosure may use a vector function that indicates a displacement from an element to a position at which a shear wave is generated, in determining a transmission condition for each element. That is, the transmission condition calculator 1110 may determine a transmission condition on the basis of a function of a plurality of displacement vectors for one or more or all of the elements. Furthermore, the transmission condition calculator 1110 may determine a transmission condition by using a pseudo inverse matrix for the function of the plurality of displacement vectors. A detailed embodiment regarding this will be described with reference to FIG. 7.

The pulse generator 1130 may generate an ultrasound signal according to a transmission condition determined by the transmission condition calculator 1110. The ultrasound signal may include a plurality of pulses based on a PRF. The pulse generator 1130 according to an embodiment of the disclosure may generate an ultrasound signal for one or more or all of the elements on the basis of a transmission condition including at least one of a phase, a level, and a delay time that are determined by the transmission condition calculator 1110.

The pulse generator 1130 according to an embodiment of the disclosure may generate an ultrasound signal which will be transmitted through the full aperture instead of a sub aperture of the transducer. Therefore, the ultrasound diagnostic apparatus 1100 enables a shear wave to be generated at a deeper internal position of an object than the sub aperture.

Figure 3:
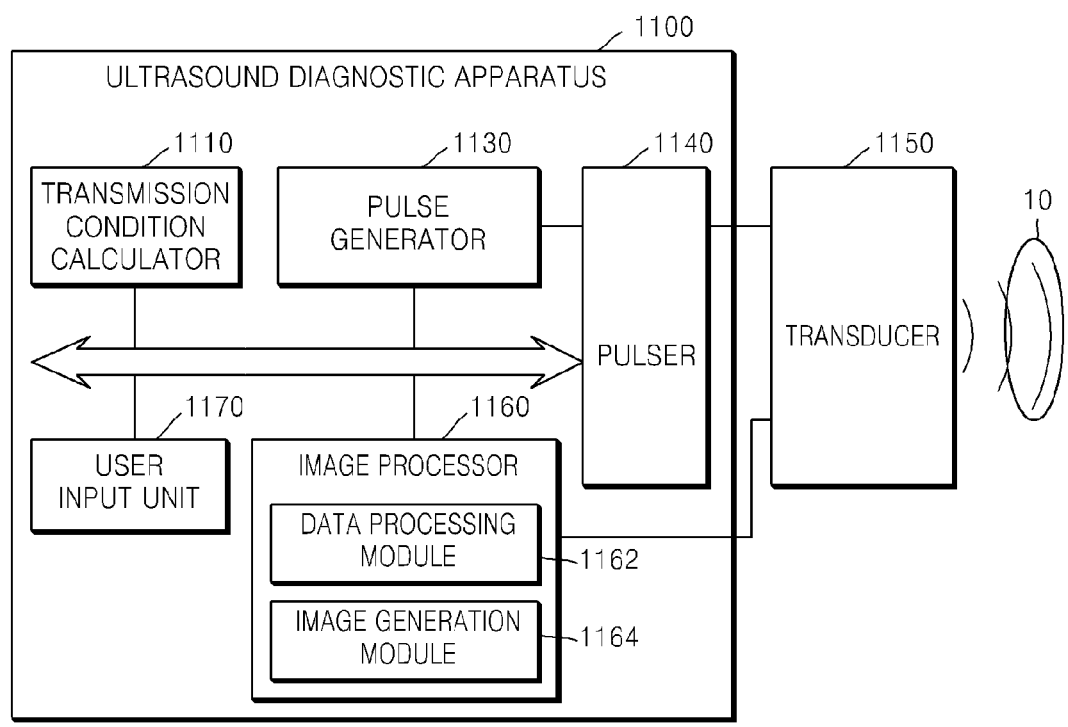
FIG. 3 is a block diagram illustrating a configuration of an ultrasound diagnostic apparatus according to another embodiment of the disclosure.

FIG. 3 is a block diagram illustrating a configuration or arrangement of an ultrasound diagnostic apparatus according to an embodiment of the disclosure. Referring to FIG. 3, the ultrasound diagnostic apparatus 1100 may further include a pulser 1140, a transducer 1150, an image processor 1160, and a user input unit 1170, in addition to the transmission condition calculator 1110 and the pulse generator 1130. The elements may be connected to each other by a system bus, for example. In FIG. 3, detailed descriptions of elements of FIG. 2 are not be repeated for the sake of brevity. Also, the ultrasound diagnostic apparatus 1100 of FIG. 3 may include some or all of the elements disclosed with respect to the ultrasound diagnostic apparatus 1000 of FIG. 1.

The pulser 1140 may apply an ultrasound signal, generated by the pulse generator 1130, to a plurality of elements included in the transducer 1150. Subsequently, the transducer 1150 may transmit the ultrasound signal to an object 10. The transducer 1150 may transmit the ultrasound signal, and moreover, sense shear waves generated at two or more internal positions of the object 10. That is, the transducer 1150 may sense a shear wave which is used to generate an elastography of the object 10.

The transducer 1150 according to an embodiment may transmit a plane wave, generated by the pulse generator 1130, to the object 10, and receive an echo signal of the plane wave for the object 10 to sense a shear wave.

The image processor 1160 may generate an internal elastography of the object 10 from a shear wave based on an ultrasound signal that is generated according to a transmission condition. The image processor 1160 according to an embodiment may include a data processing module 1162, which analyzes data of a shear wave sensed from the inside of the object 10 to measure a physical characteristic of the object 10, and an image generation module 1164 that generates an elastography obtained by image-converting the measured physical characteristic. In the embodiment, the image processor 1160 may measure, as the physical characteristic of the object 10, a traveling speed of the shear wave in the object 10, and image-convert the measured traveling speed.

The user input unit 1170 may denote a device that enables a user to input data for controlling the ultrasound diagnostic apparatus 1100, and may correspond to or be similar to the input device 500 shown in FIG. 1. For example, the user input unit 1170 may include one or more (including combinations thereof) of a keyboard, a keypad, a mouse, a touch pad, a touch screen, a trackball, a jog switch, etc, but the disclosure is not limited thereto. The user input unit 1170 according to an embodiment may receive a user input for selecting the focus distance described above with reference to FIG. 2. In the embodiment, the ultrasound diagnostic apparatus 1100 may determine a transmission condition on the basis of a focus position selected by the user input. As another example, the user input unit 1170 may further include various input devices such as a voice recognition sensor (e.g., including a microphone to receive a voice command), a gesture recognition sensor (e.g., to recognize gestures of a user including movements of a body part), a fingerprint recognition sensor, an iris recognition sensor, a depth sensor, a distance sensor, etc. The user input unit 1170 may also include, for example, a joystick, a button, a switch, an electronic pen or stylus, an output sound device (e.g., a speaker), a remote controller, a portable (e.g., a cellular or smart) phone, a tablet PC, a pedal or footswitch, a virtual-reality device, and so on. The user input unit 1170 may further include a haptic device to provide haptic feedback to a user. The user input unit 1170 may also include a touch screen, for example.

The ultrasound diagnostic apparatus 1100 having the above-described configuration or arrangement may transmit an ultrasound signal to the object 10 through the full aperture according to the determined transmission condition, thereby simultaneously generating shear waves at two or more internal positions of the object. Therefore, the ultrasound diagnostic apparatus 1100 may generate a shear wave at a deeper internal position of the object 10 when transmitting the ultrasound signal through the sub aperture.

Hereinafter, a method of diagnosing an object with shear waves by using one or more or all of the elements of the ultrasound diagnostic apparatus 1100, will be described with reference to FIGS. 4 and 5. In the flowcharts of FIGS. 4 and 5, the method includes a plurality of operations that may be sequentially performed in the transmission condition calculator 1110 and pulse generator 1130 of the ultrasound diagnostic apparatus 1100 of FIG. 2 and the pulser 1140, transducer 1150, image processor 1160, and user input unit 1170 of the ultrasound diagnostic apparatus 1100 of FIG. 3. Therefore, although some details may not be described below, it can be understood that the above description on the elements of FIGS. 2 and 3 may be applied to the flowcharts of FIGS. 4 and 5.

FIG. 4 is a flowchart illustrating an ultrasound diagnostic method according to an embodiment of the disclosure.

In operation 410, the ultrasound diagnostic apparatus 1100 may determine a transmission condition of an ultrasound signal. The ultrasound diagnostic apparatus 1100 may form multi focuses in an object, and determine the transmission condition of the ultrasound signal used to generate shear waves at two or more positions. As described above, the ultrasound diagnostic apparatus 1100 may determine at least one of a level, a phase, and a delay time of the ultrasound signal that is transmitted with each element of the transducer.

In operation 430, the ultrasound diagnostic apparatus 1100 may generate the ultrasound signal. That is, the ultrasound diagnostic apparatus 1100 may generate the ultrasound signal according to the transmission condition that is determined in operation 410. The ultrasound diagnostic apparatus 1100 may generate the ultrasound signal which will be transmitted to the object through the full aperture of the transducer, according to the transmission condition.

FIG. 5 is a flowchart illustrating an ultrasound diagnostic method according to another embodiment of the disclosure.

In operation 510, the ultrasound diagnostic apparatus 1100 may acquire information about a focus distance. The ultrasound diagnostic apparatus 1100 may acquire the information about the focus distance which may correspond to a distance from a surface of the object to a position at which a shear wave is generated, for determining the transmission condition of the ultrasound signal.

For example, the ultrasound diagnostic apparatus 1100 may receive a user input for selecting the focus distance to acquire the information about the focus distance. As another example, the ultrasound diagnostic apparatus 1100 may extract the information about the focus distance from a probe or application that is selected for diagnosing the object. That is, since a position at which a shear wave is generated is changed according to a diagnosis part or an application, the ultrasound diagnostic apparatus 1100 may acquire the information about the focus distance from an activated probe or a currently executed application.

In operation 520, the ultrasound diagnostic apparatus 1100 may determine a transmission condition. That is, the ultrasound diagnostic apparatus 1100 may determine the transmission condition on the basis of the information about the focus distance which is acquired in operation 510. The ultrasound diagnostic apparatus 1100 according to an embodiment may determine the transmission condition by using a vector function that indicates a displacement from each element of the transducer to a position at which a shear wave is generated, and the position at which the shear wave is generated may be obtained from the information about the focus distance from the surface of the object.

In operation 530, the ultrasound diagnostic apparatus 1100 may generate an ultrasound signal. That is, the ultrasound diagnostic apparatus 1100 generates the ultrasound signal for one or more or all of the elements included in the full aperture of the transducer according to the transmission condition which is determined in operation 520.

In operation 540, the ultrasound diagnostic apparatus 1100 may transmit the ultrasound signal. The ultrasound diagnostic apparatus 1100 may transmit the ultrasound signal, which is generated in operation 530, to the object through the aperture of the transducer. The ultrasound diagnostic apparatus 1100 may transmit the ultrasound signal, thereby simultaneously generating shear waves at two or more internal focuses of the object.

In operation 550, the ultrasound diagnostic apparatus 1100 may sense a shear wave which is generated in the object. That is, the ultrasound diagnostic apparatus 1100 may generate a plane wave used to sense the shear wave, transmit the plane wave to the object, and receive an echo signal of the plane wave through the transducer, thereby measuring a traveling speed of the shear wave.

In operation 560, the ultrasound diagnostic apparatus 1100 may generate an elastography. The ultrasound diagnostic apparatus 1100 may image-convert the traveling speed of the shear wave (a physical characteristic) that is sensed in operation 550, and thus generate the elastography. In the elastography, degrees of softness and stiffness in the object may be expressed in colors. The ultrasound diagnostic apparatus 1100 may display the elastography on a screen. For example, the elastography may be displayed on a screen of display unit 230, input device 500, and/or some another display which the ultrasound diagnostic apparatus 1100 transmits the elastography to, via a wired or wireless network, for example.

Figure 6:
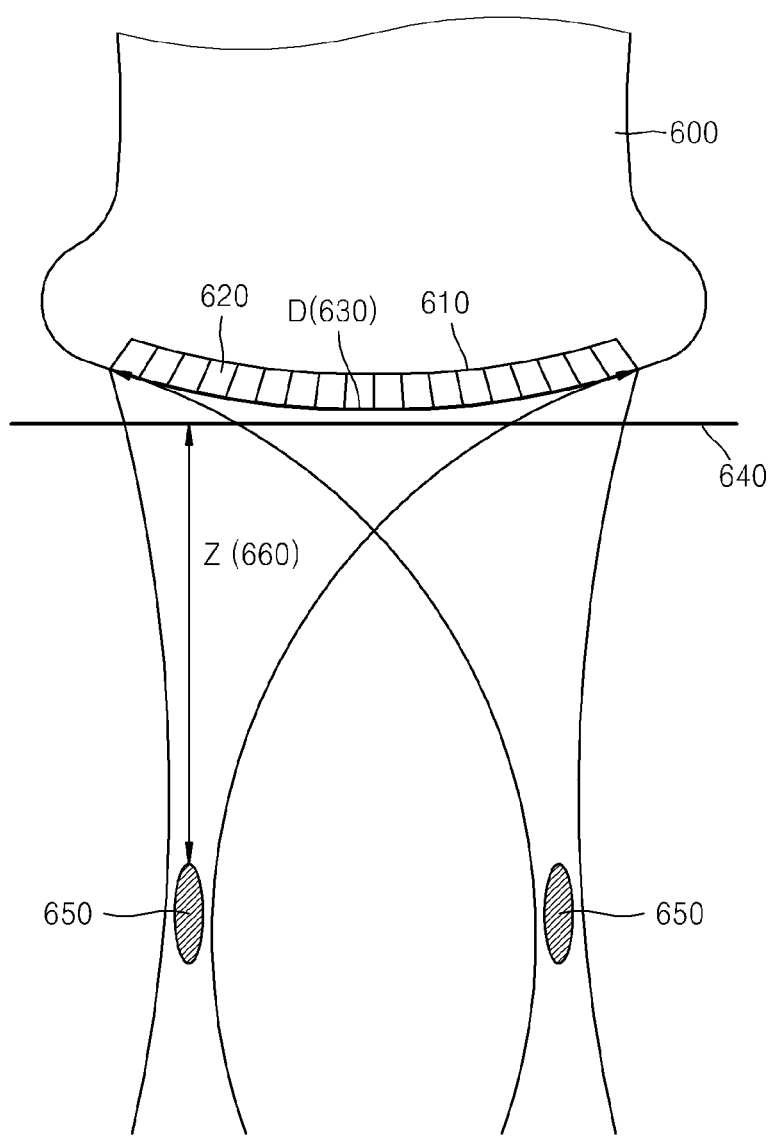
FIG. 6 is a diagram illustrating a method of generating a shear wave through a full aperture according to an embodiment of the disclosure.

FIG. 6 is a diagram illustrating a method of generating a shear wave through a full aperture according to an embodiment of the disclosure.

The ultrasound diagnostic apparatus 1100 may generate an ultrasound signal, and transmits the ultrasound signal to the inside of an object 640 through a transducer included in a probe 600. The probe 600 may be disposed near or pressed directly against the surface of the object 640. The transducer 610 may include a plurality of arranged elements 620, and may be categorized into a linear array transducer, a convex array transducer, and a phased array transducer depending on a type in which the plurality of elements 620 are arranged. For example, the elements 620 may be controlled independently of one another.

The transducer 610 may transmit and receive the ultrasound signal through an aperture 630 denoting a group of activated elements from among the plurality of elements 620. That is, the transducer 610 may transmit the ultrasound signal through a sub aperture in which some of the plurality of elements 620 are activated, or may transmit the ultrasound signal through a full aperture in which the plurality of elements 620 are all activated. In other words, the transducer 610 may transmit the ultrasound signal through a full aperture in which all of the plurality of elements 620 are activated.

An aperture that corresponds to an activated element group may be expressed as D. A focus distance 660, may correspond to a distance from a surface of the object 640 to a position 650 (e.g., disposed in internally in the object 640) at which the ultrasound signal is collected, and may be expressed as Z. Therefore, an F number denoting a relationship between an aperture and a focus distance may be expressed by Equation (1) below.

$$F = \frac{Z}{D} \quad (1)$$

The broader the aperture through which the ultrasound signal is transmitted, the lower the F number. Therefore, the ultrasound diagnostic apparatus 1100 may form a multi-focus inside the object 640 through the full aperture, and generate a shear wave at a deeper internal position of the object 640 than the sub aperture.

As described above, the ultrasound diagnostic apparatus 1100 may transmit the ultrasound signal through the full aperture according to a determined transmission condition, and a detailed example for determining a transmission condition will now be described with reference to FIG. 7.

Figure 7:
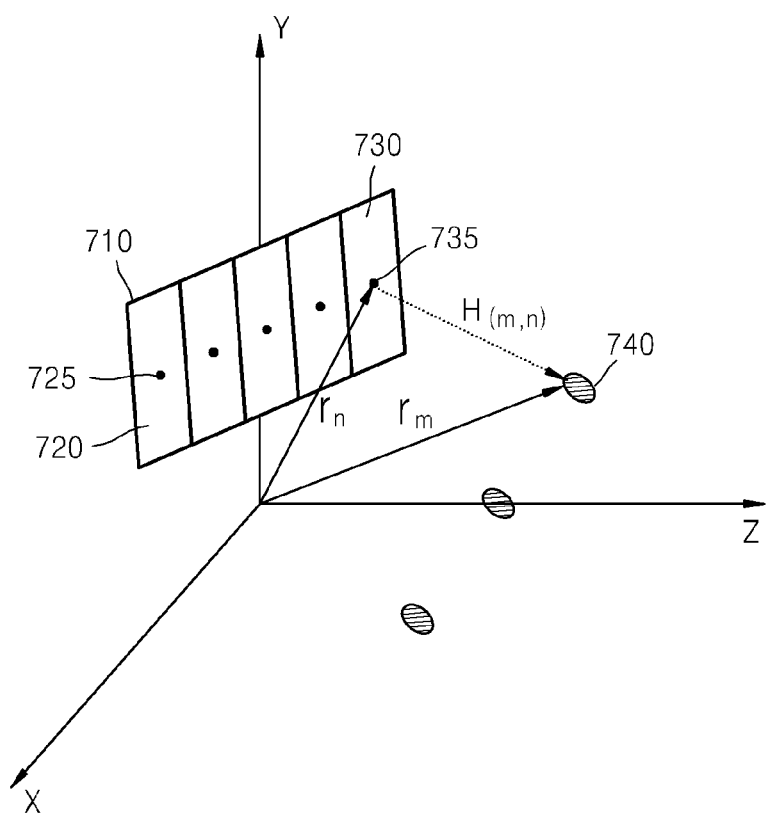
FIG. 7 is a diagram for describing an operation of calculating a transmission condition according to an embodiment of the disclosure.

FIG. 7 is a diagram for describing an operation of calculating a transmission condition according to an embodiment of the disclosure. FIG. 7 illustrates an orthogonal coordinates system that has, as the origin, an arbitrary position in a three-dimensional (3D) space.

As shown by way of example in FIG. 7, five tetragonal arrays 710 denote a transducer, and two tetragonal blocks 720 and 730 denote elements included in the transducer, respectively. A vector "rn" may denote a displacement vector from the origin to a center of a tetragonal block included in the transducer. For example, a displacement vector "rn" may correspond to a vector from the origin to the center 735 of element 730 as shown in FIG. 7, and/or may correspond to a vector from the origin to the center 725 of the element 720.

Three oval blocks 740 may denote focus positions, and denote internal positions of an object in which an ultrasound signal is collected and thus a shear wave is generated, respectively. A vector "rm" denotes a displacement vector from the origin to a focus position. The ultrasound diagnostic apparatus 1100 may acquire the vector "rm" on the basis of a focus distance. For example, a vector "rm" may correspond to a vector from the origin to the oval block 740 as shown in FIG. 7.

As described above, the ultrasound diagnostic apparatus 1100 may determine a transmission condition on the basis of a function of a plurality of displacement vectors from a plurality of elements to a position at which a shear wave is generated. The ultrasound diagnostic apparatus 1100 according to an embodiment of the disclosure may define, as expressed by Equation (2) below, a pressure at an mth focus position based on an ultrasound signal from n number of elements, through a Rayleigh-Sommerfeld integral.

$$\sum_{n=1}^{N} u_n * w_n * \frac{j*\rho*c*k}{2\pi} * \int_{S_n} \frac{e^{-j*k*|r_m-r_n|}}{|r_m-r_n|} dS_n = p(r_m) \qquad (2)$$

where "$u_n$" denotes a level, phase, and delay time of an ultrasound signal which are included in a transmission condition of the ultrasound signal, "$w_n$," denotes a coefficient which is determined for each element, and "$p(r_m)$" denotes a pressure at the mth focus position. "j" denotes an imaginary number, "p" denotes a density in a space, "c" denotes a sound speed, and "k" is a wave number and denotes "$2\pi/\lambda$". "$w_n$", which is a coefficient determined for each element, will be described in detail with reference to FIG. 8.

In Equation (2), a displacement vector from an nth element to the mth focus position may be expressed by Equation (3) below.

$$H(m, n) = \frac{j*\rho*c*k}{2\pi} * \int_{S_n} \frac{e^{-j*k*|r_m-r_n|}}{|r_m-r_n|} dS_n \qquad (3)$$

where "$S_n$" denotes a surface area of the nth element. Furthermore, the following Equation (4) may be obtained by expressing Equations (2) and (3) as a matrix.

$$Hwu=p \qquad (4)$$

where "H" denotes Equation (3), "$w_n$" denotes "$w_n$" of Equation (2), and "u" denotes "$u_n$" of FIG. 2. "p" denotes a matrix expressing pressures at m number of positions. Next, Equation (5) below may be obtained by using a relationship of "Hw=H'" in Equation (4).

$$u=H'^+p \qquad (5)$$

where "$H'^+p$" denotes a pseudo inverse matrix. That is, the ultrasound diagnostic apparatus 1100 may express "$u_n$", which is the transmission condition of the ultrasound signal, as "H(m,n)" that is a function of a plurality of displacement vectors from n number of elements to the mth focus position, and may determine the transmission condition "$u_n$" by using a pseudo inverse matrix of a matrix "H'" which is obtained by multiplying a coefficient matrix to the matrix "H". Subsequently, the ultrasound diagnostic apparatus 1100 may generate an ultrasound signal with a level, a phase, and a delay time which are determined by the transmission condition "$u_n$", and transmit the ultrasound signal, thereby generating shear waves at m number of focuses in an object.

Figure 8:
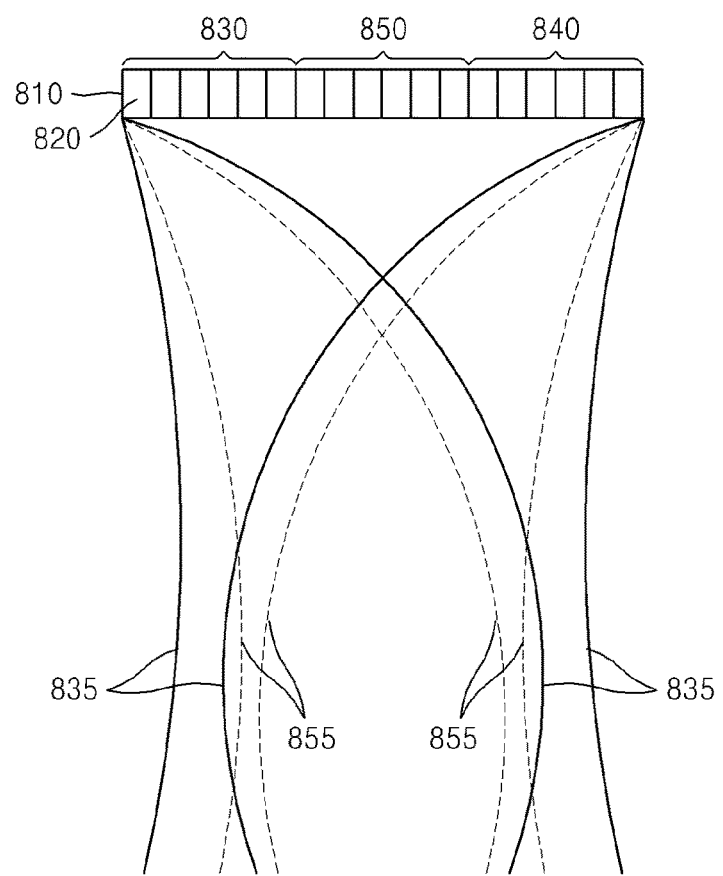
FIG. 8 is a diagram for describing an operation of calculating a transmission condition based on a position of an element according to an embodiment of the disclosure.

FIG. 8 is a diagram for describing an operation of calculating a transmission condition based on a position of an element according to an embodiment of the disclosure.

As described above with reference to FIG. 2, the ultrasound diagnostic apparatus 1100 may determine a transmission condition on the basis of a position of one or more or all of a plurality of elements 820 in a full aperture of a transducer 810. The ultrasound diagnostic apparatus 1100 may adjust the coefficient "$w_n$" described above with reference to FIG. 6 on the basis of the position of each element, and the transmission condition "$u_n$" may be determined differently for each element.

As an example, the ultrasound diagnostic apparatus 1100 may set the same coefficient for a plurality of elements included in an element group 830 and for a plurality of elements included in an element group 840 of the transducer 810. That is, the same coefficient may be set for both element group 830 and element group 840. The ultrasound diagnostic apparatus 1100 may set a lower coefficient for an element group 850 than the element groups 830 and 840. For example, the ultrasound diagnostic apparatus 1100 may set a coefficient for the elements in element group 830 and in element group 840 before setting the lower coefficient for element group 850. However, the disclosure is not so limited, and the order in which a coefficient is set for each element group may be altered. According to the above-mentioned settings, the ultrasound diagnostic apparatus 1100 may generate an ultrasound signal illustrated as a dotted line 855.

That is, the ultrasound diagnostic apparatus 1100 may set a level of an ultrasound signal, which is transmitted through the element group 850, to less than those for the element groups 830 and 840. As a result, the ultrasound diagnostic apparatus 1100 may determine different transmission conditions on the basis of positions of the respective elements in the transducer 810.

Subsequently, the ultrasound diagnostic apparatus 1100 may adjust the coefficient of the element group 850 to less than those in the above-described embodiments. Therefore, the ultrasound diagnostic apparatus 1100 may generate an ultrasound signal illustrated as a solid line 835. That is, the ultrasound diagnostic apparatus 1100 may lower a level of an ultrasound signal transmitted in the element group 850, and thus adjust a distance between focuses in addition to a depth at which a multi-focus is formed.

Above, for convenience of description, an embodiment in which a coefficient is set for each element group has been described, but the disclosure is not limited thereto. That is, the ultrasound diagnostic apparatus 1100 may set a coefficient for each element in consideration of an element position, and thus, a transmission condition of an ultrasound signal transmitted through a full aperture may be differently set for each element. For example, each individual element among the plurality of elements 820 may have a different or unique coefficient value. Alternatively, all of the elements among the plurality of elements 820 may have the same coefficient value. Alternatively, some of the elements among the plurality of elements 820 may be grouped together and assigned a first coefficient value, and some of the elements among the plurality of elements 820 may be grouped together and assigned a second coefficient value, and so on. The number of groups of elements may be more than two, and may only be limited by the total number of elements. That is, a group may include one element or more than one element. For a group of elements, the elements in that group need not be adjacent to one another. The ultrasound diagnostic apparatus 1100 may subsequently change a coefficient value for one or more or all of the elements as desired to generate an ultrasound signal having a desired distance between focuses and/or a desired depth at which the multi-focus is formed.

The ultrasound diagnostic apparatus 1100 may adjust a transmission condition on the basis of an element position, and thus improve elastography image quality, and moreover, remove artifacts that may appear in the elastography image.

Figure 9:
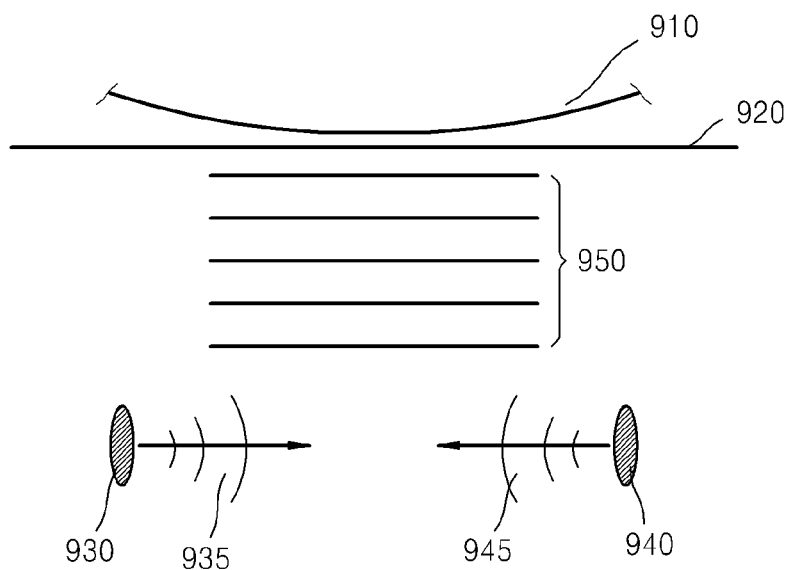
FIG. 9 is a diagram illustrating a method of sensing a shear wave according to an embodiment of the disclosure.

FIG. 9 is a diagram illustrating a method of sensing a shear wave according to an embodiment of the disclosure. As described above with reference to FIGS. 2 to 5, the ultrasound diagnostic apparatus 1100 may sense an internal shear wave of an object by using a plane wave.

First, the ultrasound diagnostic apparatus 1100 may transmit an ultrasound signal to an object 920 through a full aperture of the transducer 910, and generate shear waves 935 and 945 at internal multi focuses 930 and 940 of the object 920.

Subsequently, the ultrasound diagnostic apparatus 1100 may transmit a plane wave 950 from the transducer 910 to the inside of the object 920. The ultrasound diagnostic apparatus 1100 may receive an echo signal obtained by reflecting the plane wave 950, and measure traveling speeds of the shear waves 935 and 945 on the basis of the echo signal. The ultrasound diagnostic apparatus 1100 may generate an elastography in which the traveling speeds of the shear waves 935 and 945 are expressed in colors.

The embodiments of the disclosure may be written as computer programs including program instructions and may be implemented in general-purpose digital computers that execute the programs using a computer readable recording medium (e.g., a non-transitory computer readable recording medium). Also, a structure of data used in the aforementioned embodiments may be recorded in computer-readable recording media through various members. Program storage devices usable for describing a storage device including executable computer codes for performing various methods of the disclosure should not be understood as including transitory targets like signals. Examples of the computer readable recording medium include magnetic storage media (e.g., ROM, floppy disks, hard disks, magnetic tape, etc.) and optical recording media (e.g., CD-ROMs, or DVDs). Examples of non-transitory computer-readable media may also include magneto-optical media such as optical discs; and hardware devices that are specially configured to store and perform program instructions, such as read-only memory (ROM), random access memory (RAM), flash memory, USB memory, and the like. Examples of program instructions include both machine code, such as produced by a compiler, and files containing higher level code that may be executed by the computer using an interpreter. The program instructions may be executed by one or more processors. The described hardware devices may be configured to act as one or more software modules in order to perform the operations of the above-described embodiments, or vice versa. In addition, a non-transitory computer-readable storage medium may be distributed among computer systems connected through a network and computer-readable codes or program instructions may be stored and executed in a decentralized manner. In addition, the computer-readable storage media may also be embodied in at least one application specific integrated circuit (ASIC) or Field Programmable Gate Array (FPGA).

As described above, the ultrasound diagnostic apparatus and method determine a transmission condition for each element of a transducer, thereby generating shear waves at internal multi focuses of an object. Also, the ultrasound diagnostic apparatus and method transmit an ultrasound signal through a full aperture of the transducer, and thus generate a shear wave at an internal deeper position of the object 640 than a sub aperture.

It should be understood that the exemplary embodiments described herein should be considered in a descriptive sense only and not for purposes of limitation. Descriptions of features or aspects within an embodiment should typically be considered as available for other similar features or aspects in other embodiments. That is, different embodiments are not mutually exclusive. For example, the ultrasound diagnostic apparatus according to the disclosed embodiments may determine a transmission condition in consideration of various factors, which may be taken into account separately, or in combination with other factors. For example, the ultrasound diagnostic apparatus may determine a transmission condition in consideration of one or more of information about the focus distance, on a basis of a position of a corresponding element in the full aperture, on a basis of a function of a plurality of vectors indicating a displacement from each element to a position at which each of the shear waves is generated, and/or by using a pseudo inverse matrix of a matrix expressing the function. Moreover, any of the ultrasound diagnostic apparatuses of FIG. 1, 2, or 3 may be used to perform or implement any of the methods disclosed herein.

While one or more embodiments of the disclosure have been described with reference to the figures, it will be understood by those of ordinary skill in the art that various changes in form and details may be made therein without departing from the spirit and scope of the disclosure as defined by the following claims.

What is claimed is:
1. An ultrasound diagnostic method using shear waves, the ultrasound diagnostic method comprising:
by an ultrasound diagnostic apparatus including a transducer, the transducer comprising a plurality of elements to generate ultrasound signals:
activating all of the plurality of elements to transmit the ultrasound signals;
determining at least one transmission condition for all of the plurality of elements to form a full aperture of the plurality of elements, to transmit the ultrasound signals from the formed full aperture of the plurality of elements to at least two separate positions within an object based on the determined at least one transmission condition for all of the plurality of elements forming the full aperture; and generating the ultrasound signals from the formed full aperture, to cause the transmission of the ultrasound signals to the at least two separate positions within the object, to generate the shear waves at the at least two separate positions within the object.

2. The ultrasound diagnostic method of claim 1, wherein the determining the at least one transmission condition comprises determining the at least one transmission condition to simultaneously generate the shear waves with the ultrasound signals at the at least two separate positions inside the object.

3. The ultrasound diagnostic method of claim 1, further comprising acquiring information about at least two focus distances from a surface of the object to the at least two separate positions within the object at which each of the shear waves is generated, wherein the determining the at least one transmission condition comprises determining the at least one transmission condition based on the information about the at least two focus distances.

4. The ultrasound diagnostic method of claim 1, wherein the at least one transmission condition comprises at least one of a level, a phase, and a delay time of the ultrasound signals.

5. The ultrasound diagnostic method of claim 1, wherein the determining the at one transmission condition comprises determining the at least one transmission condition based on a position of each element of the plurality of elements in the formed full aperture.

6. The ultrasound diagnostic method of claim 1, wherein the determining the at one transmission condition comprises determining the at least one transmission condition based on a function of a plurality of vectors indicating a displacement from each element of the plurality of elements in the formed full aperture to each of the at least two separate positions at which each of the shear waves is to be generated in response to the ultrasound signals.

7. The ultrasound diagnostic method of claim 6, wherein the determining the at one transmission condition comprises determining the at least one transmission condition by using a pseudo inverse matrix of a matrix expressing the function.

8. The ultrasound diagnostic method of claim 1, further comprising:
sensing the shear waves generated at the least two positions inside the object.

9. The ultrasound diagnostic method of claim 8, wherein the sensing the shear waves comprises:
generating the ultrasound signals as plane waves to the object; and
receiving echo signals of the plane waves.

10. The ultrasound diagnostic method of claim 8, further comprising:
measuring a physical characteristic of the object based on the sensed shear waves; and
generating an elastography of the object based on the measured physical characteristic.

11. The ultrasound diagnostic method of claim 10, wherein the physical characteristic comprises a traveling speed of the shear waves.

12. A non-transitory computer-readable storage medium storing a program, that when executed, implements the ultrasound diagnostic method of claim 1 by controlling the ultrasound diagnostic apparatus including the transducer with the formed full aperture.

13. An ultrasound diagnostic apparatus to diagnose an object by using shear waves, the ultrasound diagnostic apparatus comprising:

a transducer comprising a plurality of elements to generate ultrasound signals, wherein all of the plurality of elements is activated to transmit the ultrasound signals;
a transmission condition calculator to determine at least one transmission condition for all of the plurality of elements to form a full aperture of the plurality of elements, to transmit ultrasound signals from the formed full aperture of the plurality of elements to at least two separate positions within an object based on the at least one determined transmission condition for all of the plurality of elements forming the full aperture; and
a pulse generator to generate the ultrasound signals from the formed full aperture, to cause the transmission of the ultrasound signals to the at least two separate positions within the object, to generate the shear waves at the at least two separate positions within the object,
the transmission condition calculator is implemented by one or more processors.

14. The ultrasound diagnostic apparatus of claim 13, wherein the transmission condition calculator determines the at least one transmission condition to simultaneously generate the shear waves at the at least two separate positions inside the object.

15. The ultrasound diagnostic apparatus of claim 13, wherein the transmission condition calculator acquires information about at least two focus distances from a surface of the object to at least two separate positions within the object at which each of the shear waves is generated, and determines the at least one transmission condition based on the information about the focus distance.

16. The ultrasound diagnostic apparatus of claim 13, wherein the at least one transmission condition comprises at least one of a level, a phase, and a delay time of the ultrasound signals.

17. The ultrasound diagnostic apparatus of claim 13, wherein the transmission condition calculator determines the at least one transmission condition based on a position of each element of the plurality of elements in the formed full aperture.

18. The ultrasound diagnostic apparatus of claim 13, wherein the transmission condition calculator determines the at least one transmission condition based on a function of a plurality of vectors indicating a displacement from each element of the plurality of elements in the formed full aperture to a position at which each of the shear waves is generated.

19. The ultrasound diagnostic apparatus of claim 18, wherein the transmission condition calculator determines the at least one transmission condition by using a pseudo inverse matrix of a matrix expressing the function.

20. The ultrasound diagnostic apparatus of claim 13, wherein the transducer is to sense the shear waves generated at the at least two separate positions inside the object.

21. The ultrasound diagnostic apparatus of claim 20, wherein the transducer generates the ultrasound signals as plane waves to the object, and receives echo signals of the plane waves.

22. The ultrasound diagnostic apparatus of claim 20, further comprising an image processor to measure a physical characteristic of the object based on the sensed shear waves, and to generate an elastography of the object based on the measured physical characteristic.

23. The ultrasound diagnostic apparatus of claim 22, wherein the physical characteristic comprises a traveling speed of each of the shear waves.

24. The ultrasound diagnostic apparatus of claim 13, wherein the transmission condition calculator determines the at least one transmission condition based on a respective position of each element of the plurality of elements in the formed full aperture of the transducer, and sets a coefficient for each element of the plurality of elements based on the respective position of each element of the plurality of elements, the at least one transmission condition being determined based on a value of the coefficient.

25. The ultrasound diagnostic apparatus of claim 24, wherein a first coefficient is set for a first group of elements among the plurality of elements of the transducer and the first coefficient is also set for a second group of elements among the plurality of elements of the transducer, and a second coefficient is set for a third group of elements among the plurality of elements of the transducer, the second coefficient being lower than the first coefficient.

26. The ultrasound diagnostic apparatus of claim 24, wherein the ultrasound diagnostic apparatus adjusts the coefficient to direct the transmitted ultrasound signals from the formed full aperture of the plurality of elements to the at least two separate positions inside the object, to thereby generate the shear waves at the at least two separate positions inside the object.

* * * * *